United States Patent
Hnojewyj et al.

(10) Patent No.: US 6,899,889 B1
(45) Date of Patent: May 31, 2005

(54) BIOCOMPATIBLE MATERIAL COMPOSITION ADAPTABLE TO DIVERSE THERAPEUTIC INDICATIONS

(75) Inventors: Olexander Hnojewyj, Saratoga, CA (US); Charles F. Milo, Atherton, CA (US); Gregory M Cruise, Fremont, CA (US)

(73) Assignee: NeoMend, Inc., Irvine, CA (US)

( * ) Notice: Subject to any disclaimer, the term of this patent is extended or adjusted under 35 U.S.C. 154(b) by 0 days.

(21) Appl. No.: 09/520,856

(22) Filed: Mar. 7, 2000

Related U.S. Application Data

(63) Continuation-in-part of application No. 09/283,535, filed on Apr. 1, 1999, now Pat. No. 6,458,147, which is a continuation-in-part of application No. 09/188,083, filed on Nov. 6, 1998, now Pat. No. 6,371,975.

(51) Int. Cl.[7] .......................... A61K 47/42; A61L 17/10; C08L 89/00
(52) U.S. Cl. ...................... 424/426; 424/486; 525/54.1; 606/214
(58) Field of Search ................................. 528/354, 355, 528/357, 361; 606/213, 214, 216; 436/164; 424/426, 443, 444, 448, 486, 489, 490, 491, 492, 499; 128/898; 514/2, 8, 12, 21; 525/54.1, 54.2, 408, 415

(56) References Cited

U.S. PATENT DOCUMENTS

| | | | |
|---|---|---|---|
| 4,101,380 A | 7/1978 | Rubinstein et al. | 195/63 |
| 4,161,948 A | 7/1979 | Bichon | 428/305 |
| 4,464,468 A | 8/1984 | Avrameas et al. | 435/177 |
| 4,839,345 A | 6/1989 | Doi et al. | 514/21 |
| 5,051,292 A | 9/1991 | Katoh et al. | 428/141 |
| 5,051,406 A | 9/1991 | Satoh | 514/21 |
| 5,129,882 A | 7/1992 | Weldon et al. | 604/96 |
| 5,207,670 A | 5/1993 | Sinofsky | 606/8 |
| 5,252,714 A | 10/1993 | Harris et al. | 530/391.9 |

(Continued)

FOREIGN PATENT DOCUMENTS

| | | |
|---|---|---|
| WO | WO 93/17669 | 9/1993 |
| WO | WO 94/03155 | 2/1994 |
| WO | WO 96/11671 | 10/1994 |
| WO | WO 96/21469 | 7/1996 |
| WO | WO 97/22371 | 6/1997 |
| WO | WO 99/07417 | 8/1997 |
| WO | WO 98/12274 A1 * | 3/1998 |
| WO | WO 00/09087 | 8/1998 |
| WO | WO 00/09199 | 8/1998 |
| WO | WO 98/35631 | 8/1998 |
| WO | Wo 00/33764 | 12/1998 |
| WO | WO 99/14259 | 3/1999 |
| WO | WO 99/31167 | 6/1999 |
| WO | WO 99/45964 | 9/1999 |
| WO | WO 00/62827 | 10/2000 |

OTHER PUBLICATIONS

Kurisawa, M. et al. "Double–stimuli–responsive degradation of hydrogels consisting of oligopeptide–terminated poly(ethylene glycol) and dextran with an interpenetrating polymer network"; Journal of Biomaterials Science, Polymer Edition, vol. 8, No. 9, 1997, pp. 691–708.

Nimni M.E. et al; "Chemically modified collagen: A natural biomaterial for tissue replacement"; Journal of Biomedical Materials Research, vol. 21, No. 6, Jun. 1987 pp. 741–771.

Transactions: Society for Biomaterials: "Protedytically Degradable Hydrogels": West et al (1997) TAB L.

*Primary Examiner*—Jeffrey Edwin Russel
(74) *Attorney, Agent, or Firm*—Ryan Kromholz & Manion, S.C.

(57) ABSTRACT

A biocompatible material genus serves as the foundation for multiple material composition species, each adapted to a specific therapeutic indication.

15 Claims, 5 Drawing Sheets

U.S. PATENT DOCUMENTS

| | | | | |
|---|---|---|---|---|
| 5,318,524 A | | 6/1994 | Morse et al. | 604/82 |
| 5,383,896 A | | 1/1995 | Gershony et al. | 606/213 |
| 5,403,278 A | | 4/1995 | Ernst et al. | 604/60 |
| 5,410,016 A | | 4/1995 | Hubbell et al. | 528/354 |
| 5,419,765 A | | 5/1995 | Welden et al. | 604/96 |
| 5,514,379 A | | 5/1996 | Weissleder et al. | 424/426 |
| 5,520,885 A | | 5/1996 | Coelho et al. | 422/101 |
| 5,529,577 A | | 6/1996 | Hammerslag | 606/214 |
| 5,567,435 A | | 10/1996 | Hubbell et al. | 424/426 |
| 5,583,114 A | | 12/1996 | Barrows et al. | 514/21 |
| 5,601,602 A | | 2/1997 | Fowler | 606/213 |
| 5,618,790 A | * | 4/1997 | Kennedy et al. | 514/12 |
| 5,626,601 A | | 5/1997 | Gershony et al. | 606/194 |
| 5,626,863 A | | 5/1997 | Hubbell et al. | 424/426 |
| 5,653,730 A | | 8/1997 | Hammerslag | 606/214 |
| 5,672,662 A | | 9/1997 | Harris et al. | 525/408 |
| 5,676,689 A | | 10/1997 | Kensey et al. | 606/213 |
| 5,725,498 A | | 3/1998 | Janzen et al. | 604/51 |
| 5,733,563 A | | 3/1998 | Fortier | 424/422 |
| 5,739,208 A | | 4/1998 | Harris | 525/54.1 |
| 5,759,194 A | | 6/1998 | Hammerslag | 606/214 |
| 5,782,860 A | | 7/1998 | Epstein et al. | 606/213 |
| 5,791,352 A | | 8/1998 | Reich et al. | 606/213 |
| 5,824,015 A | | 10/1998 | Sawyer | 606/214 |
| 5,843,124 A | | 12/1998 | Hammerslag | 606/214 |
| 5,844,016 A | | 12/1998 | Sawhney et al. | 522/13 |
| 5,858,746 A | | 1/1999 | Hubbell et al. | 435/177 |
| 5,874,500 A | | 2/1999 | Rhee et al. | 525/54.1 |
| 5,900,245 A | | 5/1999 | Sawhney et al. | 424/426 |
| 5,900,461 A | | 5/1999 | Harris | 525/54.11 |
| 5,922,009 A | | 7/1999 | Epstein et al. | 606/213 |
| 5,932,462 A | | 8/1999 | Harris et al. | 435/188 |
| 5,935,147 A | | 8/1999 | Kensey et al. | 606/213 |
| 5,936,035 A | | 8/1999 | Rhee et al. | 525/54.1 |
| 5,942,209 A | | 8/1999 | Leavitt et al. | 424/1.45 |
| 5,951,583 A | | 9/1999 | Jensen et al. | 606/194 |
| 5,951,589 A | | 9/1999 | Epstein et al. | 606/213 |
| 5,986,043 A | | 11/1999 | Hubbell et al. | 528/354 |
| 5,990,237 A | | 11/1999 | Bentley et al. | 525/54.2 |
| 6,007,613 A | | 12/1999 | Izoret | 106/160.1 |
| 6,022,361 A | | 2/2000 | Epstein et al. | 606/151 |
| 6,033,424 A | | 3/2000 | Ouchi | 606/205 |
| 6,033,427 A | | 3/2000 | Lee | 606/213 |
| 6,051,248 A | | 4/2000 | Sawhney et al. | 424/426 |
| 6,083,524 A | | 7/2000 | Sawhney et al. | 424/426 |
| 6,152,943 A | | 11/2000 | Sawhney | 606/193 |
| 6,162,241 A | | 12/2000 | Coury et al. | 606/214 |
| 6,165,201 A | | 12/2000 | Sawhney et al. | 606/214 |
| 6,177,095 B1 | | 1/2001 | Sawhney et al. | 424/426 |
| 6,179,862 B1 | | 1/2001 | Sawhney | 606/214 |
| 6,371,975 B2 | * | 4/2002 | Cruise et al. | 606/214 |
| 6,458,147 B1 | * | 10/2002 | Cruise et al. | 606/214 |

* cited by examiner

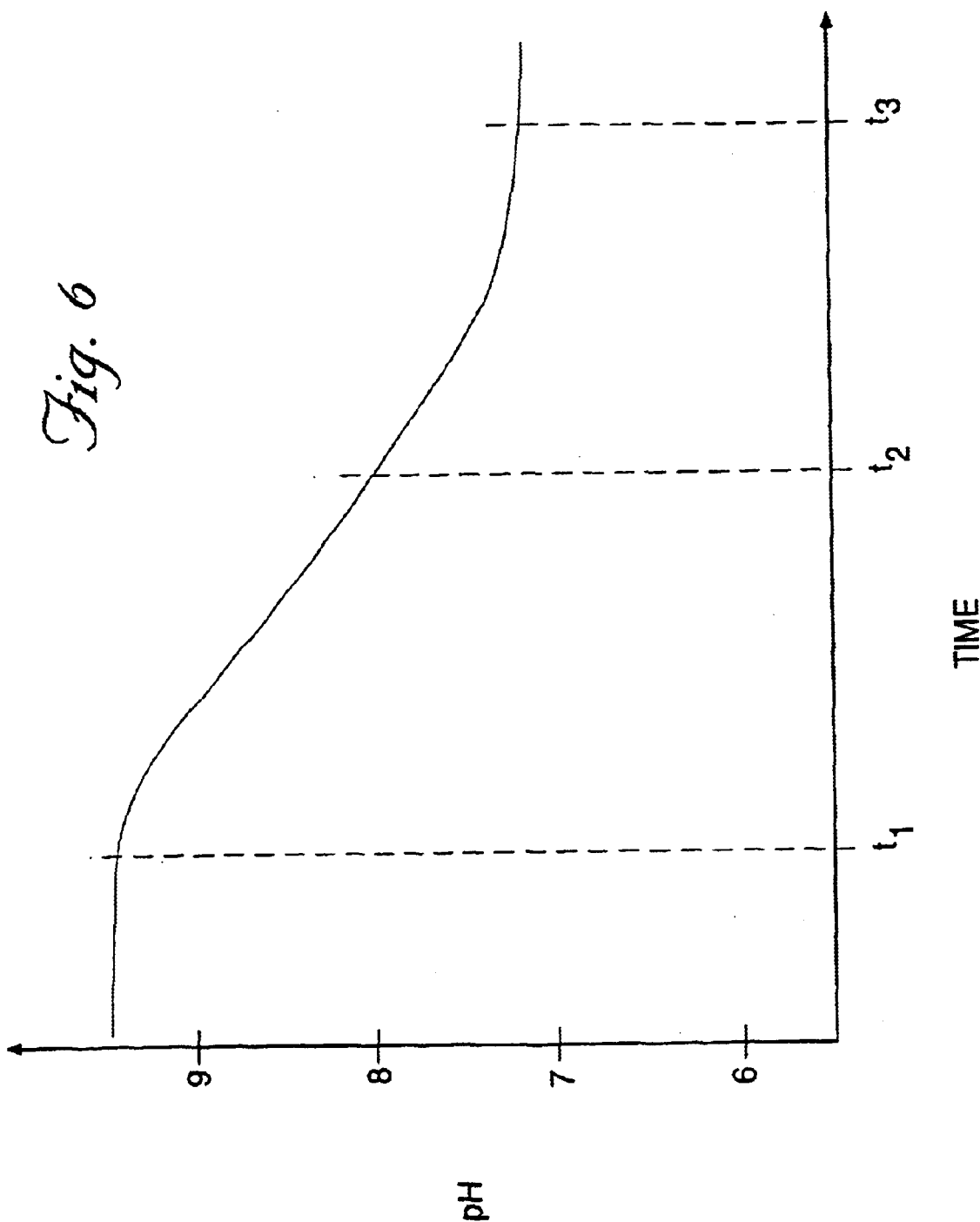

BIOCOMPATIBLE MATERIAL COMPOSITION ADAPTABLE TO DIVERSE THERAPEUTIC INDICATIONS

RELATED APPLICATION

This application is a continuation-in-part of U.S. patent application Ser. No. 09/283,535, filed Apr. 1, 1999, and entitled "Compositions, Systems, and Methods for Arresting or Controlling Bleeding or Fluid Leakage in Body Tissue," now U.S. Pat. No. 6,458,147, which is itself a continuation-in-part of U.S. patent application Ser. No. 09/188,083, filed Nov. 6, 1998 and entitled "Compositions, Systems, and Methods for Creating In Situ, Chemically Cross-Linked, Mechanical Barriers, now U.S. Pat. No. 6,371,975."

FIELD OF THE INVENTION

The invention generally relates to the composition of biocompatible materials and their application to body tissue to affect desired therapeutic results.

BACKGROUND OF THE INVENTION

There are many therapeutic indications today that pose problems in terms of technique, cost efficiency, or efficacy, or combinations thereof.

For example, following an interventional procedure, such as angioplasty or stent placement, a 5 Fr to 8 Fr arteriotomy remains. Typically, the bleeding from the arteriotomy is controlled through pressure applied by hand, by sandbag, or by C-clamp for at least 30 minutes. While pressure will ultimately achieve hemostasis, the excessive use and cost of health care personnel is incongruent with managed care goals.

As another example, blood leaks from a variety of different tissues are common during surgical procedures. Examples include following trauma to or resection of the liver, spleen, or kidney, vascular anastomoses, and bone bleeding during sternotomy. Presently, the surgeon has a limited number of options to control bleeding, typically pressure, thrombin, fibrin glue, bone wax, and/or collagen sponge.

Likewise, controlling air leaks from lung tissue is difficult to achieve during thoracic procedures. Examples include lung resections and lung volume reduction surgery. Presently, the surgeon has a limited number of options to control air leaks, typically a chest tube is required to remove air from the thoracic cavity. The presence of a chest tube extends the stay of the patient in the hospital. If the air leaks could be sealed at the time of surgery, the patient would be able to be discharged sooner.

Similarly, controlling liquid leaks from tissue is difficult to achieve during surgical procedures. Examples include dural leaks and lymph fluid leaks during surgical procedures. Typically, the surgeon does not control dural leaks due to the lack of an effective dural substitute, potentially increasing the risk of transmission of infectious agents. Controlling solid leaks from tissue is likewise difficult to achieve during surgical procedures. Examples include bowel leaks during surgical procedures. Typically, the surgeon controls bowel leaks by adding additional sutures until the leak is no longer observed.

As another example, adhesions are abnormal, fibrous connections of tissues that are not normally connected. Adhesions are formed as a part of the normal wound healing response of tissue, however they can result in infertility and pain. Several products are available for use by the surgeon to prevent the formation of adhesions, however the efficacy of the marketed products has not been conclusively demonstrated.

Likewise, tissue voids can be created by a variety of procedures. For example, the ABBI™ system, marketed by United States Surgical Company, is a minimally invasive breast biopsy system that cores out breast tissue for analysis by a pathologist. The cores range in size from five to twenty millimeters in diameter. Following the removal of the core, a tissue void is created and the surrounding tissue oozes blood into the void.

Various tissues can also be augmented to create a more desired appearance. For example, an injectable bovine collagen, marketed by Inamed Corporation, can be used to reduce the appearance of facial wrinkles or create the appearance of fuller lips. While the treatment is effective, the persistence is brief.

The treatment of arterio-venous malformations (AVM's) and aneurysms provide further examples. AVM's are tangled masses of blood vessels that are neither arteries nor veins, commonly found in the brain, possibly leading to hemorrhagic stroke. Clinically, AVM's are treated by surgical removal. Before removal, the AVM must be embolized to prevent uncontrolled bleeding. Aneurysms are abnormal widening of portions of blood vessels, leading to an increased chance of rupture. Clinically, aneurysms are treated by surgical removal, stent-grafting, or coils. Another possible treatment modality is to fill the ballooned section of the blood vessel with a biomaterial, protecting and strengthening the diseased tissue.

There is also an increasing trend towards site-specific delivery of pharmaceuticals and vectors. The main advantage is high dose delivery at the diseased tissue, but a low systemic dose. For example, a depot filled with anti-cancer agents can be placed directly on a tumor. The areas surrounding the depot have a high concentration of the anti-cancer agent, but the systemic dose is low, minimizing side effects.

Cells, as well as pharmaceuticals and vectors, can be likewise delivered to a diseased tissue site. The cells could be genetically modified, autologous, or derived from other sources.

There remains a demand for biomaterials that improve the technique, cost efficiency, and efficacy of these and other therapeutic indications.

SUMMARY OF THE INVENTION

One aspect of the invention provides a biocompatible genus material composition upon which a diverse family of biocompatible material composition species can be created. The species are remarkably well adapted to specific therapeutic indications, although the therapeutic indications themselves differ significantly.

In one embodiment, the genus biocompatible material comprises a mixture of a protein solution and a polymer solution. The polymer solution includes a derivative of a hydrophilic polymer with a functionality of at least three. Upon mixing, the protein solution and the polymer solution cross-link to form a non-liquid, three-dimensional network.

In one embodiment, the network degrades over time back to a liquid form. In this embodiment, the polymer includes a degradation control region selected to achieve a desired degradation period. The degradation control region can be selected to form different species, each having a different degradation period. The degradation periods can vary, e.g., within a range of between about 1 day to greater than 500 days.

In one embodiment, the polymer includes a cross-linking group selected to achieve a desired cross-linking period. The cross-linking group can be selected to achieve different species, each having its own desired cross-linking period. The cross-linking periods can vary, e.g., within a range of from less than one second to greater than 10 hours.

In one embodiment, the polymer includes both a degradation control region and a cross-linking group. In this embodiment, each region can be individually selected to form different species, each species having its own period of degradation and cross-linking customized to achieve one or more therapeutic objectives.

Another aspect of the invention provides systems making use of the diverse species for different therapeutic indications. Each system includes instructions for forming a mixture of the protein solution and polymer solution and for applying the mixture to accomplish a particular therapeutic objective. The particular therapeutic objective can be, e.g., sealing a vascular puncture site, sealing tissue from blood or gas or liquid leaks, sealing tissue from solid leaks, preventing post operative adhesions, repairing a tissue void, augmenting tissue, embolizing an arterio-venous malformation, filling an aneurysm, delivering a pharmaceutical, or delivering cells.

Another aspect of the invention provides a biocompatible material comprising a mixture of a protein solution and a polymer solution which, upon mixing, cross-link to form a non-liquid, three-dimensional network. The material includes an agent that undergoes color change in response to cross-linking of the mixture.

In one embodiment, the agent undergoes color change in response to change in pH during cross-linking.

In one embodiment, the agent exhibits a first color when the mixture is in a liquid state and a second color, different than the first color, when the mixture forms the non-liquid, three-dimensional network.

In one embodiment, the agent exhibits a first color when the mixture is in transition between a liquid state and the non-liquid, three dimensional network, and a second color, different than the first color, when the mixture forms the non-liquid, three-dimensional network.

Features and advantages of the inventions are set forth in the following Description and Drawings, as well as in the appended claims.

BRIEF DESCRIPTION OF THE DRAWINGS

FIG. 6 is a graph showing the changes on pH as a given species composition cross-links to form a solid three-dimensional network.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

I. Overview

Figure 1:
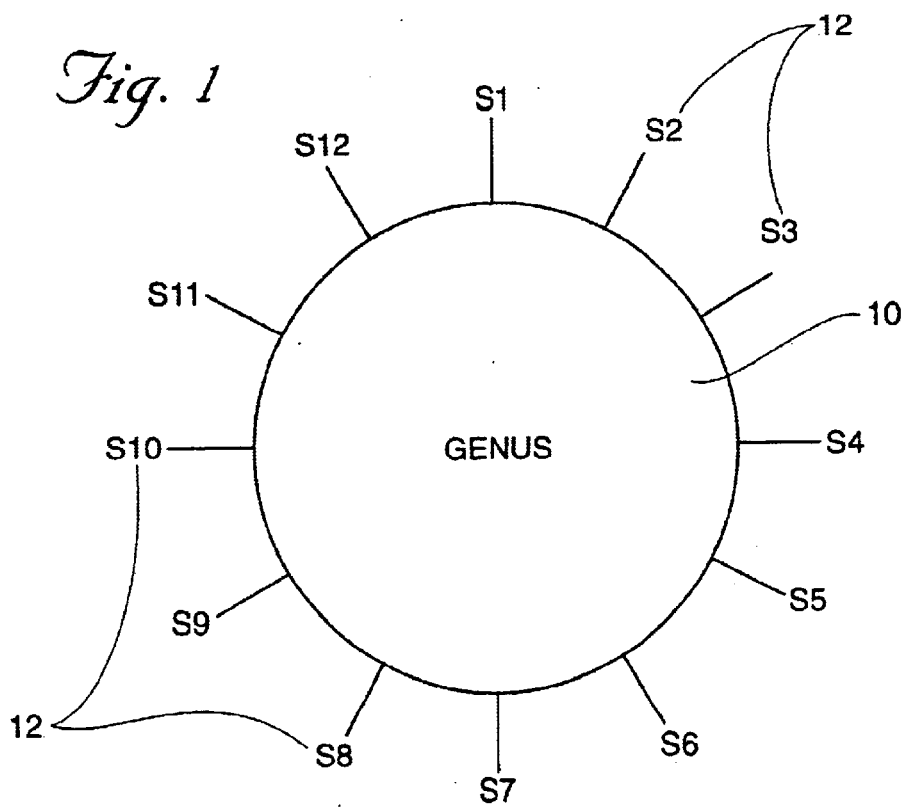
FIG. 1 is a diagrammatic view of a genus composition of a biocompatible material that forms the basis for multiple composition species, each well adapted to a specific therapeutic indication.

FIG. 1 shows a genus composition 10 comprising a biocompatible material. The genus composition 10 is the basis for multiple material composition species 12.

The material composition species 12 of the genus composition 10 share several common fundamental characteristics, including:

(i) each composition species 12 is capable of being created in situ by mixing basic formative components, at least two of which are common throughout the genus;

(ii) the formative components, upon mixing, are capable of transforming from a liquid state to a biocompatible solid state (in a process called "gelation");

(iii) after gelation, the solid composition exhibits desired mechanical properties including adhesive strength, cohesive strength, and elasticity;

(iv) after gelation, the solid composition is also capable of transforming over time by physiological mechanisms from the solid state to a biocompatible liquid state, which can be cleared by the body (in a process called "degradation"); and (v) each of the characteristics (ii) to (iv) can be selectively and independent controlled within wide physical ranges.

The common fundamental characteristics of the genus 10 give rise to a diverse family of biocompatible material composition species 12, having differing rates of gelation, rates of degradation, and mechanical properties. The species are remarkably well adapted to specific therapeutic indications, although the therapeutic indications themselves differ significantly.

In the illustrated embodiment (see FIG. 1), the genus 10 is shown, by way of example, to contain twelve distinct species 12, each having a corresponding different therapeutic indication, as also listed in the following Table.

TABLE 1

Biocompatible Material Composition Species and Corresponding Therapeutic Indications

| Species | Therapeutic Indication |
|---|---|
| 1 | Sealing Vascular Puncture Sites |
| 2 | Sealing Tissue From Blood Leaks |
| 3 | Sealing Tissue From Gas Leaks |
| 4 | Sealing Tissue From Liquid Leaks |
| 5 | Sealing Tissue From Solid Leaks |
| 6 | Preventing Post-Operative Adhesions |
| 7 | Repair of Tissue Voids |
| 8 | Augmentation of Tissue |
| 9 | Embolization of Arterio-Venous Malformations (AVM) |
| 10 | Filling of Aneurysms |
| 11 | Delivery of Pharmaceuticals |
| 12 | Delivery of Cells |

Figure 2:
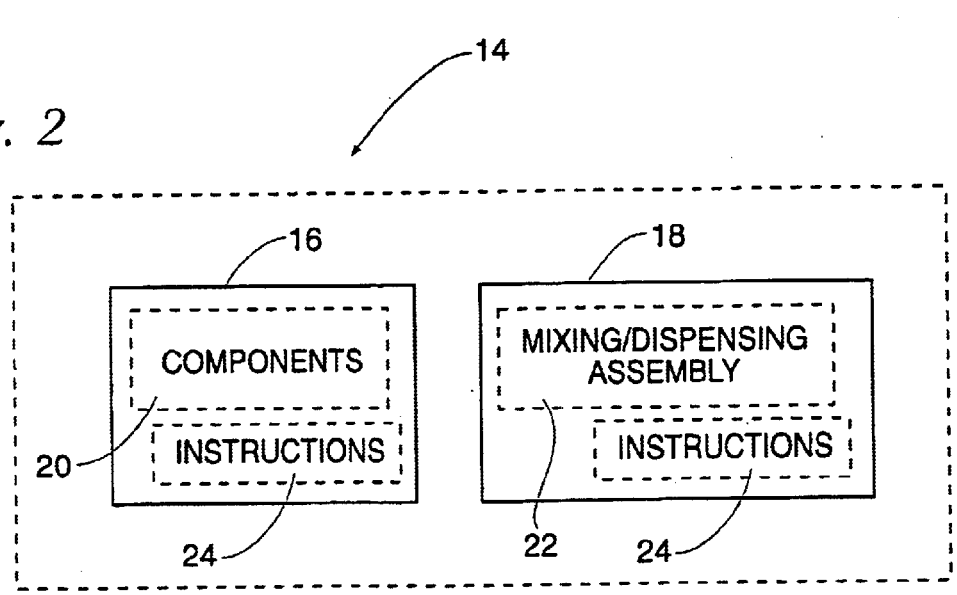
FIG. 2 is a diagrammatic view of a system comprising first and second functional kits useful for applying or delivering a given composition species shown in FIG. 1 at the intended delivery site.

As FIG. 2 shows, the common fundamental characteristics of the composition genus 10 make possible the development of a family of systems 14 for applying or delivering the species 12 at the intended treatment site. Each delivery system 14 shares certain common features, because of characteristics common to the genus composition 10. Nevertheless, the delivery systems 14 also differ in specific respects, because each species 12 is tailored to meet the needs of a particular desired therapeutic indication.

Due to the common fundamental characteristics (i) and (ii) of the genus 10, each delivery system can be consolidated into two functional kits 16 and 18. The first kit 16 contains the basic formative components 20 of the genus composition 10. The kit 16 stores the basic formative components 20 in an unmixed condition prior to use. Certain aspects of the formative components 20 differ, according to the species 12 that the system 14 delivers or applies. Still, the fundamental characteristic of holding the basic formative components 20 in an unmixed condition until the instance of use is common to all delivery systems 14 of the family.

The second kit 18 contains a mixing/dispensing assembly 22 for each species 12. The mixing/dispensing assembly 22 brings the formative components 20 into intimate mixing contact in liquid form. The mixing/dispensing assembly 22 dispenses the liquid mixture to the intended therapeutic site, where the liquid mixture transforms in situ to a solid form. Among the delivery systems 14, certain aspects of the mixing/dispensing assembly 22 differ, according to requirements of the particular therapeutic indication. Still, the fundamental characteristic of the mixing of the formative components 20 for in-situ delivery is common to all delivery systems 14.

One or both kits 16 and 18 preferably includes instructions 24 for forming the liquid mixture and dispensing the liquid through the mixing/dispensing assembly 22 to achieve the particular desired therapeutic indication.

II. The Genus Material Composition

In a preferred embodiment, the genus material composition 10 creates a non-liquid, three-dimensional network, termed a hydrogel. In this embodiment, there are two fundamental formative components common to the genus 10; namely, (i) a protein and (ii) a polymer.

The hydrogel is created by the reaction between one or more nucleophilic (electron donator) groups on one of the components (either the protein or the polymer) and one or more electrophilic (electrode withdrawing) groups on the other one of the components. The polymer can include one or more nucleophilic groups, such as amine groups (—NH2), or thiol groups (—SH), or one or more electrophilic groups, such as alcohol groups (—OH) or carboxyl groups (—COOH), or combinations thereof. Likewise, the sequence of amino acids forming the protein (which determines the protein's bioactivity) can provide nucleophilic reactivity (e.g., lysine, arginine, asparagine, glutamine, or cysteine), or can provide electrophilic reactivity (e.g., aspartic acid, glutamic acid, serine, threonine, or tyrosine), or both. The amino acid sequence of the protein can thus dictate the selection of the polymer, and vice versa. The protein component most preferably takes the form of a protein solution with nucleophilic groups. The polymer component most preferably takes the form of a solution of an electrophilic derivative of a hydrophilic polymer with a functionality of at least three. In this arrangement, the electrophilic groups on the polymer react with the nucleophilic groups on the protein, to form the hydrogel.

Use of these two fundamental components permit the rates of gelation and degradation to be accurately and predictably controlled, to create a variety of different species 12. Furthermore, a genus material composition 10 based upon these two fundamental components possesses desirable mechanical properties, which can also be accurately and selective manipulated among the species. The ability to accurately and selectively control the rate of gelation, the rate of degradation, and the mechanical properties, allows the creation of diverse species, each optimized to meet the requirements of a particular therapeutic indication.

A. The Fundamental Protein Component

Suitable protein solutions for incorporation into the genus material 10 include non-immunogenic, hydrophilic proteins. Examples include serum, serum fractions, and solutions of albumin, gelatin, antibodies, fibrinogen, and serum proteins. In addition, water soluble derivatives of hydrophobic proteins can be used. Examples include solutions of collagen, elastin, chitosan, and hyaluronic acid. In addition, hybrid proteins with one or more substitutions, deletions, or additions in the primary structure may be used.

Furthermore, the primary protein structure need not be restricted to those found in nature. An amino acid sequence can be synthetically designed to achieve a particular structure and/or function and then incorporated into the genus material. The protein can be recombinantly produced or collected from naturally occurring sources.

The preferred protein solution is 25% human serum albumin, USP. Human serum albumin is preferred due to its biocompatibility and its ready availability.

B. The Fundamental Polymer Component

The fundamental polymer component of the genus material composition is a hydrophilic, biocompatible polymer that is electrophilically derivatized with a functionality of at least three. Examples include poly(ethylene glycol), poly (ethylene oxide), poly(vinyl alcohol), poly (vinylpyrrolidinone), poly(ethyloxazoline), and poly (ethylene glycol)-co-poly (propylene glycol) block copolymers.

The fundamental polymer component is not restricted to synthetic polymers, as polysaccharides, carbohydrates, and proteins could be electrophilically derivatized with a functionality of at least three. In addition, hybrid proteins with one or more substitutions, deletions, or additions in the primary structure may be used as the polymer component. In this arrangement, the protein's primary structure is not restricted to those found in nature, as an amino acid sequence can be synthetically designed to achieve a particular structure and/or function and then incorporated into the material. The protein of the polymer component can be recombinantly produced or collected from naturally occurring sources.

Preferably, the polymer component is comprised of poly (ethylene glycol) (PEG) with a molecular weight between 1,000 and 30,000 g/mole, more preferably between 2,000 and 15,000, and most preferably between 10,000 and 15,000 g/mole. PEG has been demonstrated to be biocompatible and non-toxic in a variety of physiological applications. The preferred concentrations of the polymer are 5% to 35% w/w, more preferably 5% to 20% w/w. The polymer can be dissolved in a variety of aqueous solutions, but water is preferred.

The preferred polymer can be generally expressed as compounds of the formula:

PEG-(DCR-CG)$_n$

Where:

DCR is a degradation control region.

CG is a crosslinking group.

$n \geq 3$

While the preferred polymer is a multi-armed structure, a linear polymer with a functionality, or reactive groups per molecule, of at least three can also be used. The utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

The uses of PEG polymers with functionality of greater than three provides a surprising advantage. When crosslinked with higher functionality PEG polymers, the concentration of albumin can be reduced to 25% and below. Past uses of difunctional PEG polymers require concentrations of albumin well above 25%, e.g. 35% to 45%. Use of lower concentrations of albumin result in superior tissue sealing properties with increased elasticity, a further desired result. Additionally, 25% human serum albumin, USP is commercially available from several sources, however higher concentrations of human serum albumin, USP are not commercially available. By using commercially available materials, the dialysis and ultrafiltration of the albumin solution, as disclosed in the prior art, is eliminated, significantly reducing the cost and complexity of the preparation of the albumin solution.

C. The Resulting Genus 10 Hydrogel Composition

Upon mixing the fundamental protein solution component with the fundamental polymer solution, the non-liquid, three-dimensional network (i.e., the hydrogel) is formed.

To minimize the liberation of heat during the crosslinking reaction, the concentration of the crosslinking groups of the fundamental polymer component is preferably kept less than 5% of the total mass of the reactive solution, and more preferably about 1% or less. The low concentration of the crosslinking group is also beneficial so that the amount of the leaving group is also minimized. In a typical clinical application, about 50 mg of a non-toxic leaving group is produced during the crosslinking reaction, a further desired result. In a preferred embodiment, the CG comprising an N-hydroxysuccinimide ester has demonstrated ability to participate in the crosslinking reaction with albumin without eliciting adverse immune responses in humans.

The genus material composition is well tolerated by the body, without invoking a severe foreign body response. Over a controlled period, the material is degraded by physiological mechanisms. Histological studies have shown a foreign body response consistent with a biodegradable material, such as VICRYL™ sutures. As the material is degraded, the tissue returns to a quiescent state. The molecules of the degraded genus hydrogel composition are cleared from the bloodstream by the kidneys and eliminated from the body in the urine. In a preferred embodiment of the invention, the material loses its physical strength during the first fifteen days, and totally resorbs in about four weeks.

III. Creating the Species Compositions

Species compositions are created from the genus composition by controlling the rate of gelation, or controlling the rate of degradation, or controlling the mechanical properties, or combinations thereof. The controlled properties of the species permit the use of the genus 10 material composition in diverse therapeutic indications.

A. Controlling the Rate of Gelation

The rate of gelation is optimally controlled by the selection of the crosslinking group (CG) and the reaction pH. The concentration of the CG in the polymer solution, and the concentration of nucleophilic groups in the protein solution also can be used to control the rate of gelation, however changes in these concentrations typically result in changes in the mechanical properties of the hydrogel, as well as the rate of gelation.

The electrophilic CG is responsible for the crosslinking of the albumin, as well as binding the hydrogel to the surrounding tissue. The CG can be selected to selectively react with thiols, selectively react with amines, or react with thiols and amines. CG's that are selective to thiols include vinyl sulfone, N-ethyl maleimide, iodoacetamide, and orthopyridyl disulfide. CG's that are selective to amines include aldehydes. Non-selective electrophilic groups include active esters, epoxides, oxycarbonylimidazole, nitrophenyl carbonates, tresylate, mesylate, tosylate, and isocyanate. The preferred CG's are active esters, more preferred, an ester of N-hydroxysuccinimide. The active esters are preferred since they react rapidly with nucleophilic groups and have a non-toxic leaving group.

The rate of gelation can also be controlled by the selection of the reaction pH. At a lower pH, a larger fraction of nucleophilic groups is unavailable for reaction with the electrophile. At higher pH's, a larger fraction of nucleophilic groups is available for reaction with the electrophile. Ultimately, pH controls the concentration of nucleophilic groups that are available for reaction. The reaction pH is a useful mechanism to control the rate of gelation as it controls the rate without affecting the mechanical properties of the resulting hydrogel.

The reaction pH is optimally controlled by the buffer composition and concentration. Preferred buffer systems are sodium phosphate and sodium carbonate, which can alone or in combination provide high or low pH buffers. A high pH buffer is preferred when high rates of gelation are desired. A low pH buffer is preferred for slower rates of gelation. The buffer concentration also plays a significant role in the rate of gelation. Because of the crosslinking, a leaving group is formed. In the preferred embodiment, the leaving group is acidic. So as the reaction proceeds, the pH drops and the rate of gelation slows. At higher buffer concentrations, the fast rate of gelation is sustained over the length of the reaction. At lower concentrations, the buffer system is saturated and no longer functions.

Through the selection of the CG and the reaction pH, the transformation of the material from a liquid to a solid can be controlled from less than 1 second to greater than 10 hours, more preferably less than 1 second to 10 minutes, and most preferably less than 1 second to 2 minutes.

It may be desirable to monitor the progression of the cross-linking. For example, when using Species 1 (to seal vascular puncture sites), it is desirable to know when the composition is semi-solid, which indicates that it is time to remove the catheter/introducer and apply pressure to the puncture site. It is also desirable to next know when the composition is solid, which indicates that pressure to the puncture site can be removed. The transitions from liquid to semi-solid and then from semi-solid to solid can be determined by timing the reaction.

The pH of the composition (protein and polymer) changes as cross-linking progresses (see FIG. 6). The change in pH during cross-linking for a given composition can be empirically determined using a spectophotometer. The pH is high (e.g., pH 9 to 10) when the polymer is liquid (time $t_1$ in FIG. 6). The pH is lower (e.g., pH 7) (time $t_3$ in FIG. 6) when the composition is solid. The pH is at an intermediate value (e.g., pH 8) when the composition is in transition between liquid and solid (time $t_3$ in FIG. 6). The composition can include one or more colorimetric pH indicators to indicate, by color changes, the progression of the gelation.

For example, xylenol blue exhibits a purple color at pH 9–10, a yellow color at pH 8, and a yellow color at pH 7. Phenol red exhibits a red color at pH 9–10, a red color at pH 8, and a yellow color at pH 7. By including a mixture of xylenol blue and phenol red in the composition, the composition, as it cross-links, will exhibit a purple/blue color (mixture of purple and red) at time t, (pH greater than 9), indicating a liquid state; an orange color (mixture of yellow and red) at time $t_2$ (pH about 8), indicating a semi-solid state; and a yellow color (mixture of yellow and yellow) at time $t_3$ (pH about 8), indicating a solid state.

As another example (in which lower pH values can be differentiated), phenolphthalein or o-cresolphthalein exhibit a red color at pH 9–10 and exhibit are clear color (i.e., are "colorless") at pH 8 and below. Bromothymol blue exhibits a blue color at pH 7 and above, and a yellow color at pH 6 and below. By including a mixture of phenolphthalein (or o-cresolphthalein) and bromothymol blue, the composition, as it cross-links, will exhibit a purple/reddish color (mixture of purple and red) when the pH is greater than 9, indicating a liquid state; a blue color (mixture of clear and blue) when the pH is about 8), indicating a semi-solid state; and a yellow color (mixture of clear and yellow) when the pH is about 6–7, indicating a solid state.

B. Controlling the Rate of Degradation

The rate of degradation is controlled by the degradation control region (DCR), the concentration of the CG's in the polymer solution, and the concentration of the nucleophilic groups in the protein solution. Changes in these concentrations also typically result in changes in the mechanical properties of the hydrogel, as well as the rate of degradation.

The rate of degradation is best controlled by the selection of the chemical moiety in the degradation control region, DCR. If degradation is not desired, a DCR can be selected to prevent biodegradation or the material can be created without a DCR. However, if degradation is desired, a hydrolytically or enzymatically degradable DCR can be selected. Examples of hydrolytically degradable moieties include saturated di-acids, unsaturated di-acids, poly (glycolic acid), poly(DL-lactic acid), poly(L-lactic acid), poly($\xi$-caprolactone), poly($\delta$_valerolactone), poly($\gamma$-butyrolactone), poly(amino acids), poly(anhydrides), poly (orthoesters), poly(orthocarbonates), and poly (phosphoesters). Examples of enzymatically degradable DCR's include SEQ ID NO 1 Leu-Gly-Pro-Ala (collagenase sensitive linkage) and Gly-Pro-Lys (plasmin sensitive linkage). It should also be appreciated that the DCR could contain combinations of degradable groups, e.g. poly (glycolic acid) and di-acid.

Through the selection of the DCR, the transformation of the material from a solid hydrogel to a degraded liquid can be controlled from as little as 1 day to greater than 500 days, more preferably 5 days to 30 days.

C. Controlling the Mechanical Properties

Desired mechanical properties of the hydrogel include cohesive strength, adhesive strength, and elasticity. Through the selection of the functionality, concentration, and molecular weight of the protein and polymer, the mechanical properties of the hydrogel can be adjusted to suit a variety of clinical needs.

The mechanical properties of the hydrogel are controlled, in part, by the number of crosslinks in the hydrogel network as well as the distance between crosslinks. Both the number of crosslinks and the distance between crosslinks are dependent on the functionality, concentration, and molecular weight of the polymer and the protein.

Functionality, or the number of reactive groups per molecule, affects the mechanical properties of the resulting hydrogel by influencing both the number of and distance between crosslinks. As discussed previously, the utility of a given polymer significantly increases when the functionality is increased to be greater than or equal to three. The observed incremental increase in functionality occurs when the functionality is increased from two to three, and again when the functionality is increased from three to four. By increasing the functionality of the polymer or protein at a constant concentration, the concentration of crosslinking groups available for reaction are increased and more crosslinks are formed. However, increased mechanical properties cannot be controlled with functionality alone. Ultimately, the steric hindrances of the protein or polymer to which the reactive groups are attached predominate and further changes in the mechanical properties of the hydrogel are not observed. The effect of functionality is saturated when the functionality reaches about four.

The concentration of the protein and polymer also affect the mechanical properties of the resulting hydrogel by influencing both the number of and distance between crosslinks. Increasing the protein and polymer concentration increases the number of available crosslinking groups, thereby increasing the strength of the hydrogel. However, decreases in the elasticity of the hydrogel are observed as the concentration of the protein and polymer is increased. The effects on the mechanical properties by concentration are limited by the solubility of the protein and polymer.

The polymer and protein molecular weight affects the mechanical properties of the resulting hydrogel by influencing both the number of and distance between crosslinks. Increasing the molecular weight of the protein and polymer decreases the number of available crosslinking groups, thereby decreasing the strength of the hydrogel. However, increases in the elasticity of the hydrogel are observed with increasing molecular weight of the protein and polymer. Low molecular weight proteins and polymers result in hydrogels that are strong, but brittle. Higher molecular weight proteins and polymers result in weaker, but more elastic gels. The effects on the mechanical properties by molecular weight are limited by the solubility of the protein and polymer. However, consideration to the ability of the body to eliminate the polymer should be made, as large molecular weight polymers are difficult to clear.

IV. Exemplary Species Compositions

It should be appreciated that by adjusting the rate of gelation, the mechanical properties of the resulting hydrogel, and the rate of degradation, the genus material composition can be adapted for use in a variety of medical indications.

The following species compositions and their therapeutic indications are included by way of example.

A. Species 1: Sealing of Vascular Puncture Sites

For sealing vascular puncture sites, a biomaterial formulation with a gelation time of fifteen to sixty seconds is preferred, more preferably fifteen to thirty seconds. This period allows the biomaterial to be delivered through the delivery device and flow into the surface irregularities before solidification. The period before solidification also enhances patient safety when compared to alternatives in the prior art.

Collagen plugs or slurries have been previously used to seal vascular puncture sites. However, if the collagen plug or slurry enters the vasculature, emboli downstream from the arteriotomy is a distinct possibility. In contrast, preclinical studies have demonstrated that emboli do not form if the a biomaterial of the Species 1 enters the bloodstream before solidification. Biomaterial of the Species 1 is diluted in flowing blood to a point where emboli cannot be formed.

Furthermore, the rate of gelation is reduced at the pH of flowing blood, further enhancing the dilution effect.

For this indication, the hydrogel Species 1 possesses sufficient adhesive strength to prevent dislodging from the arteriotomy. The hydrogel Species 1 also has sufficient cohesive strength to prevent rupture under arterial pressure, i.e., up to about 200 mm Hg. The hydrogel Species 1 also seals the arteriotomy for up to 15 days post-application before loss of mechanical properties through degradation, and completely degrades by 30 days post-application.

The following is a representative composition for Species 1:

Polymer component: 17% w/w 4-arm poly(ethylene glycol) tetra-succinimidyl glutarate, MW 10,000 in water for injection.

Protein component: 25% w/w human serum albumin, USP supplemented with 300 mM dibasic sodium phosphate, USP.

B. Species 2: Sealing Tissue from Blood Leaks

Preclinical studies have demonstrated that a biomaterial of Species 2 is effective in controlling diffuse organ bleeding. The bleeding is not controlled via physiological interactions with the clotting cascade, but rather the biomaterial of Species 2 mechanically seals the tissue to control the bleeding.

For this indication, the biomaterial formulation of the Species 2 possesses an instantaneous gelation time. To achieve hemostasis in this indication, the biomaterial Species 2 solidifies before being removed from the site by gravity and/or diluted by flowing blood. The resulting hydrogel Species 2 also possesses sufficient adhesive strength to prevent dislodging from the wound and sufficient cohesive strength to prevent rupture under arterial pressure, up to about 200 mm Hg. The hydrogel Species 2 seals the wound for up to 15 days post-application before loss of mechanical properties through degradation, and completely degrades by 30 days post-application.

The following is a representative composition for Species 2:

Polymer component: 17% w/w 4-arm poly(ethylene glycol) tetra-succinimidyl succinate, MW 10,000 in water for injection.

Protein component: 25% w/w human serum albumin, USP supplemented with 250 mM sodium carbonate and 50 mM sodium bicarbonate.

C. Species 3: Sealing Tissue from Gas Leaks

Preclinical studies have demonstrated that Species 3 is effective in controlling air leaks from the lung. The biomaterial of Species 3 forms a mechanical barrier over the suture or staple line.

In this indication, the biomaterial of Species 3 possesses an instantaneous gelation time. To achieve sealing in this indication, the biomaterial solidifies before being removed from the site by gravity. The resulting hydrogel Species 3 possesses sufficient adhesive strength to prevent dislodging from the wound and sufficient cohesive strength to prevent rupture under physiological lung pressure. Hydrogel Species 3 also exhibits sufficient elasticity to withstand repeated lung inflation. The hydrogel Species 3 seals the wound for up to 15 days post-application before loss of mechanical properties through degradation, and completely degrades by 30 days post-application.

The following is a representative composition for Species 3:

Polymer component: 17% w/w 4-arm poly(ethylene glycol) tetra-succinimidyl succinate, MW 10,000 in water for injection.

Protein component: 25% w/w human serum albumin, USP supplemented with 250 mM sodium carbonate and 50 mM sodium bicarbonate.

D. Species 4: Sealing Tissue from Liquid Leaks

To seal a liquid leak, the biomaterial of Species 4 forms a mechanical barrier over the wound, suture, or staple line. The biomaterial of Species 4 possesses an instantaneous gelation time, to solidify before being removed from the site by gravity. The resulting hydrogel Species 4 exhibits sufficient adhesive strength to prevent dislodging from the wound and sufficient cohesive strength to prevent rupture under physiological pressure. The hydrogel Species 4 seals for up to 15 days post-application before loss of mechanical properties through degradation and completely degrades by 30 days post-application.

The following is a representative composition for Species 4:

Polymer component: 17% w/w 4-arm poly(ethylene glycol) tetra-succinimidyl succinate, MW 10,000 in water for injection.

Protein component: 25% w/w human serum albumin, USP supplemented with 250 mM sodium carbonate and so mM sodium bicarbonate.

E. Species 5: Sealing Tissue from Solid Leaks

To seal a solid leak, the biomaterial of Species 5 forms a mechanical barrier over the wound, suture, or staple line. The biomaterial of Species 5 has an instantaneous gelation time, to solidify before being removed from the site by gravity.

The resulting hydrogel Species 5 has sufficient adhesive strength to prevent dislodging from the wound and sufficient cohesive strength to prevent rupture under physiological pressure. The hydrogel Species 5 seals the wound for up to 15 days post-application before loss of mechanical properties through degradation, and is completely degraded by 30 days post-application.

The following is a representative composition for Species 5:

Polymer component: 17% w/w 4-arm poly(ethylene glycol) tetra-succinimidyl succinate, MW 10,000 in water for injection.

Protein component: 25% w/w human serum albumin, USP supplemented with 250 mM sodium carbonate and 50 mM sodium bicarbonate.

F. Species 6: Prevention of Post-Operative Adhesions

The biomaterial of Species 6 coats the injured tissue surface, preventing the deposition of fibrin, and allows the formation of a new layer of epithelial cells. For the prevention of post-operative adhesions, the biomaterial of Species 6 is capable of being laparoscopically delivered, and possesses an instantaneous gelation time. For this indication, the biomaterial Species 6 solidifies before being removed from the site by gravity.

The resulting hydrogel Species 6 has sufficient adhesive strength to prevent dislodging from the wound. The hydrogel Species 6 adheres to the tissue for three to fifteen days post-application, preferably seven to ten days, before significant amounts of degradation occur. The biomaterial of Species 6 completely degrades in five to 180 days post-application, preferably five to thirty days.

The following is a representative composition for Species 6:

Polymer component: 9% w/w 4-arm poly(ethylene glycol) tetra-succinimidyl succinate, MW 10,000 in water for injection.

Protein component: 13% w/w human serum albumin, USP supplemented with 250 mM sodium carbonate and 50 mM sodium bicarbonate.

G. Species 7: Repair of Tissue Voids

The biomaterial of Species 7 fills the tissue void and solidifies. For repair of tissue voids, a biomaterial of Species 7 possesses a gelation time of approximately 5 seconds. The five second gelation time allows the formulation to enter the void, fill surface irregularities, achieve hemostasis, and prevent the formation of air pockets inside the hydrogel. The resulting hydrogel Species 7 has sufficient adhesive strength to prevent dislodging from the void and sufficient cohesive strength to prevent rupture under venous pressure, up to 100 mm Hg. The hydrogel Species 7 seals the wound for up to 15 days post-application before loss of mechanical properties through degradation and completely degraded by 30 to 60 days post-application.

The following is a representative composition for Species 7:

Polymer component: 17% w/w 4-arm poly(ethylene glycol) tetra-succinimidyl glutarate, MW 10,000 in water for injection.

Protein component: 25% w/w human serum albumin, USP supplemented with 100 mM sodium carbonate and 50 mM sodium bicarbonate.

H. Species 8: Augmentation of Tissue

The biomaterial of Species 8 enhances the desired tissue and solidifies. For tissue augmentation, the biomaterial of Species 8 has a gelation time of approximately 120 seconds, to allow the formulation to enter the surface irregularities, to prevent the formation of air pockets inside the hydrogel, and to allow the user to add or subtract volume to achieve the desired effect.

The resulting hydrogel Species 8 has sufficient adhesive strength to prevent dislodging from the tissue site. The hydrogel Species 8 does not degrade for up to one year post-application.

The following is a representative composition for Species 8:

Polymer component: 17% w/w 4-arm poly(ethylene glycol) tetra-propionic acid succinimidyl ester, MW 10,000 in water for injection.

Protein component: 25% w/w human serum albumin, USP

I. Species 9: Embolization of Arterio-Venous Malformations (AVM's)

The biomaterial of Species 9 is delivered as a liquid, but quickly sets up to a solid, embolizing the AVM. For embolization of AVM's, the biomaterial of Species 9 has a gelation time of approximately 30 to 120 seconds. The time before solidification allows the biomaterial of Species 9 to fill the tortuous mass of blood vessels completely.

The resulting hydrogel Species 9 has sufficient adhesive strength to prevent dislodging from the tissue site. The degradation of the hydrogel Species 9 is not relevant, as the AVM is removed immediately after embolization.

The following is a representative composition for Species 9:

Polymer component: 17% w/w 4-arm poly(ethylene glycol) tetra-succinimidyl glutarate, MW 10,000 in water for injection.

Protein component: 25% w/w human serum albumin

J. Species 10: Filling of Aneurysms

The biomaterial of Species 10 is delivered as a liquid, but quickly sets up to a solid to fill the aneurysm. For aneurysm filling, the biomaterial of Species 10 exhibits a gelation time of approximately 5 to 30 seconds. The time before solidification allows the formulation to fill the aneurysm completely.

The resulting hydrogel Species 10 has sufficient adhesive strength to prevent dislodging from the aneurysm and sufficient cohesive strength to prevent rupture under arterial pressure, up to about 200 mm Hg. The hydrogel Species 10 does not degrade for up to one year post-application.

The following is a representative composition for Species 10:

Polymer component: 17% w/w 4-arm poly(ethylene glycol) tetra-propionic acid succinimidyl ester, MW 10,000 in water for injection.

Protein component: 25% w/w human serum albumin, USP supplemented with 100 mM sodium carbonate and 50 mM sodium bicarbonate.

K. Species 11: Delivery of Pharmaceuticals

The biomaterial of Species 11 serves as the depot for the pharmaceutical or vector. The resulting hydrogel Species 11 can be solidified directly on the diseased tissue. For delivery of pharmaceuticals, a biomaterial of Species 11 has a gelation time of approximately 5 to 30 seconds. The resulting hydrogel Species 11 has sufficient adhesive strength to prevent dislodging from the tissue and sufficient cohesive strength to prevent fragmentation. The degradation of the hydrogel Species 11 is dependent on the desired time frame for release of the pharmaceutical, ranging from 1 week to 1 year.

The following is a representative composition for Species 11:

Polymer component: 17% w/w 4-arm poly(ethylene glycol) tetra-succinimidyl glutarate, MW 10,000 in water for injection.

Protein component: 25% w/w human serum albumin supplemented with 75 mM sodium carbonate and 75 mm sodium bicarbonate.

L. Species 12: Delivery of Cells

The biomaterial of Species 12 serves as the matrix for the cells to be delivered. For delivery of cells, the biomaterial of Species 12 has a gelation time of approximately 5 to 30 seconds.

The resulting hydrogel Species 12 has sufficient adhesive strength to prevent dislodging from the tissue and sufficient cohesive strength to prevent fragmentation. The degradation of the hydrogel Species 12 is dependent on the desired time frame for the cells to remodel the tissue, ranging from 1 week to 6 months.

The following is a representative composition for Species 12:

Polymer component: 17% w/w 4-arm poly(ethylene glycol) tetra-succinimidyl glutarate, MW 10,000 in water for injection.

Protein component: 25% w/w human serum albumin supplemented with 75 mM sodium carbonate and 75 mM sodium bicarbonate.

The following Table summarizes the gelation time, degradation time, and mechanical properties of the species 1 to 12 the composition genus 10.

TABLE 2

Principal Characteristics and Therapeutic Indications of Species 1 to 12 of the Fundamental Genus Composition

| Species | Gelation Time | Degradation Time | Mechanical Properties | Therapeutic Indication |
|---|---|---|---|---|
| 1 | 15 to 60 Seconds | 30 Days | Adhesive Strength: Prevent Dislodgment Cohesive Strength: Prevent Rupture Under | Sealing of Vascular Puncture Sites |

TABLE 2-continued

Principal Characteristics and Therapeutic Indications of Species 1 to 12 of the Fundamental Genus Composition

| Species | Gelation Time | Degradation Time | Mechanical Properties | Therapeutic Indication |
|---|---|---|---|---|
| 2 | Instantaneous | 30 Days | Adhesive Strength: Prevent Dislodgment Cohesive Strength: Prevent Rupture Under Arterial Pressure | Sealing Tissue from Blood Leaks |
| 3 | Instantaneous | 30 days | Adhesive Strength: Prevent Dislodgment Cohesive Strength: Prevent Rupture under Lung Pressure Elasticity: To Withstand Repeated Lung Inflation | Sealing Tissue from Gas Leaks |
| 4 | Instantaneous | 30 days | Adhesive Strength: Prevent Dislodgment Cohesive Strength: Prevent Rupture under Physiologic Pressure | Sealing Tissue from Liquid Leaks |
| 5 | Instantaneous | 30 days | Adhesive Strength: Prevent Dislodgment Cohesive Strength: Prevent Rupture under Physiologic Pressure | Sealing Tissue from Solid Leaks |
| 6 | Instantaneous | 5 to 30 Days | Adhesive Strength: Prevent Dislodgment | Prevention of Post Operative Adhesions |
| 7 | 5 Seconds | 30 to 60 Days | Adhesive Strength: Prevent Dislodgment Cohesive Strength: Prevent Rupture under Venous Pressure | Repair of Tissue Voids |
| 8 | 120 seconds | 1 Year | Adhesive Strength: Prevent Dislodgment | Augmentation of Tissue |
| 9 | 30 to 120 seconds | N/A | Adhesive Strength: Prevent Dislodgment | Embolization of AVM's |
| 10 | 5 to 30 Seconds | 1 Year | Adhesive Strength: Prevent Dislodgment Cohesive Strength: Prevent Rupture Under Arterial Pressure | Filling of Aneurysms |
| 11 | 5 to 30 Seconds | 1 Year | Adhesive Strength: Prevent Dislodgment Cohesive Strength: Prevent Fragmentation | Delivery of Pharmaceuticals |
| 12 | 5 to 30 seconds | 1 week to 6 months | Adhesive Strength: Prevent Dislodgment Cohesive Strength: Prevent Fragmentation | Delivery of Cells |

VI. General Methodology for Species Development

Figure 5:
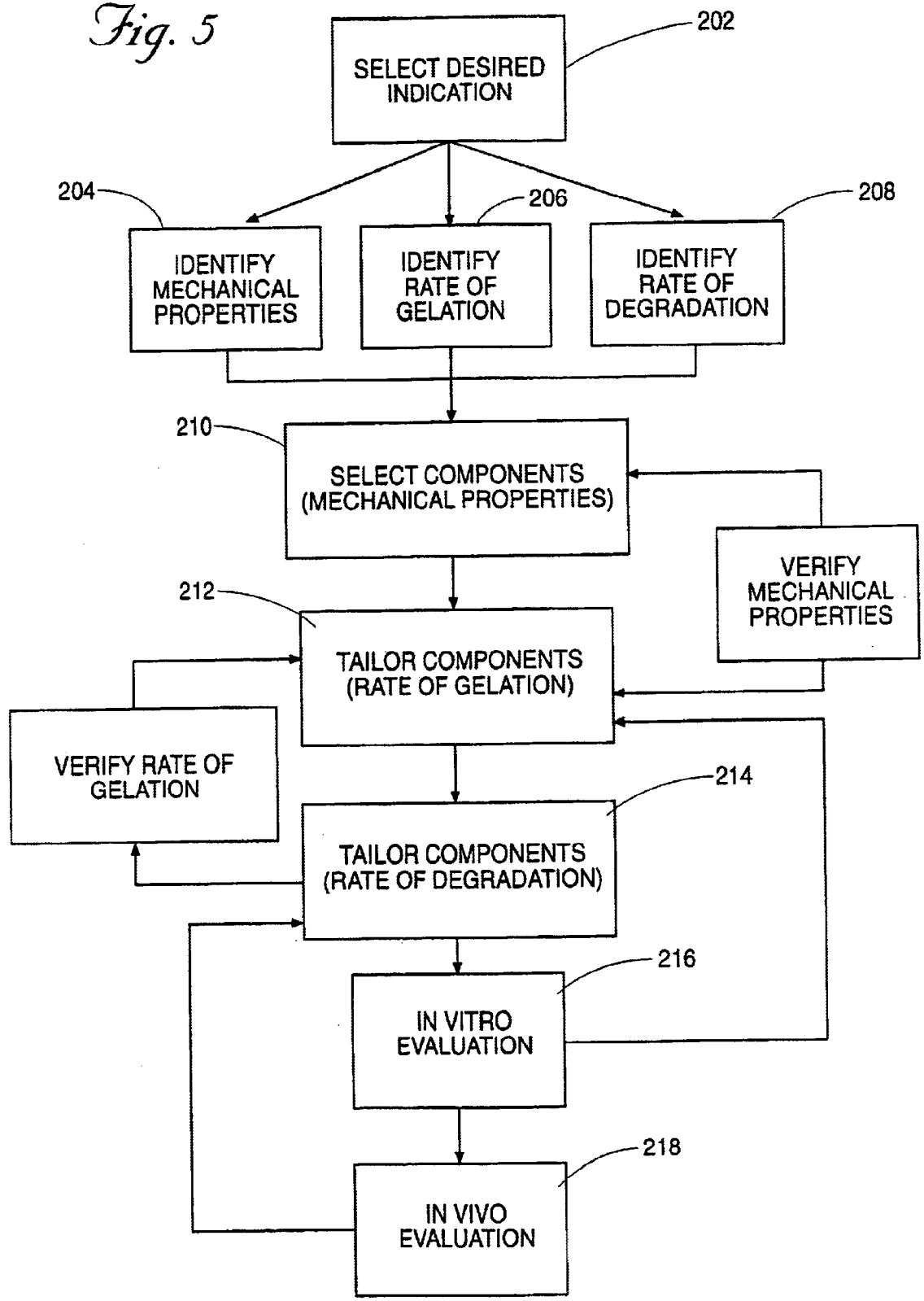
FIG. 5 is a flowchart illustrating a methodology for developing species compositions based upon the composition genus shown in FIG. 1.

FIG. 5 shows a flowchart illustrating a methodology 200 for developing species compositions based upon the composition genus 10.

The first step 202 is to select a desired clinical indication. Based upon the therapeutic requirements of the selected clinical indication, steps 204, 206, and 208 are followed to identify, respectively, the mechanical properties, the rate of gelation, and the rate of degradation suited for the indication.

Upon identifying the mechanical properties desired for the indication, a step 210 is carried out to selectively select the components of the composition genus 10, so as to create a species having the desired mechanical properties. As discussed previously, the mechanical properties can be selected through the concentration of the protein and the polymer. Elasticity can be obtained through lower concentrations of the protein and the polymer and increasing molecular weight of the polymer. Cohesive strength can be obtained through higher concentrations of the protein and the polymer and decreasing molecular weight of the polymer. Increased adhesive strength can be obtained by increasing the ratio of the concentration of polymer to the concentration of the protein. Until the buffer system is fully optimized, the evaluation of the mechanical properties at this step 210 should be performed after a suitable cross-linking period, to allow completion of the crosslinking reaction.

Once the desired mechanical properties have been achieved, a step 212 can be carried out to further selectively tailor the components of the composition genus 10 to create for the species the desired rate of gelation. As discussed previously, the rate of gelation can be selected with the buffer system and the cross-linking group of the polymer. Increased rates of gelation can be achieved by using carbonate buffers, higher pH's, and higher buffer concentrations. Decreased rates of gelation can be achieved by using phosphate buffers, lower pH's, and lower buffer concentrations. Once the desired rate of gelation has been obtained, it should be verified that the desired mechanical properties are still present during the clinically relevant period.

Once the desired mechanical properties and rate of gelation have been achieved, a step 214 can be carried out to further selectively tailor the components of the composition genus 10 to create for the species the desired rate of degradation. As discussed previously, the rate of degradation can be selected by changing the degradation control region on the polymer portion of the genus composition. Increased rates of degradation can be achieved by using glycolide or lactide, while decreased rates of degradation can be achieved by using glutaric acid as the degradation control region. A formulation that does not degrade can also be achieved by elimination of the degradation control region. Once the desired rate of degradation has been obtained, it should be verified that the desired mechanical properties and rate of gelation are still maintained.

A step 216 can now be conducted to evaluate the species in in vitro models, if available. These models are used to verify the mechanical properties and rate of gelation in a clinically relevant manner. If the results indicate that these properties need to be adjusted, they can be refined.

A final step 218 comprises in vivo experimentation. In the in vivo experimentation, the biocompatibility, effectiveness, and rate of degradation of the species are confirmed.

VII. Exemplary Delivery Systems

The delivery systems 14 serve to mix the fundamental protein and polymer solution components intimately, using atomization, static mixers, or in-line channel mixing. The mixing technique employed depends upon the requirements of the particular therapeutic indication, and, in particular, the gelation time and morphology of the treatment site.

A typical delivery system 14 for the genus material composition (see FIG. 3) includes, in the first kit 16, first and second dispensing syringes 60 and 62, in which the formative components of the genus material composition are contained.

The first dispensing syringe 60 contains a concentration of buffered protein solution component 100. The protein solution is supplemented with the appropriate buffers, sterile filtered, aseptically filled into the syringe 60, and the syringe 60 is capped for storage prior to use.

The second dispensing syringe 62 contains an inert, electrophilic, water soluble polymer component 102. The polymer component 102 is initially packaged prior to use in the second dispensing syringe 62 in an inert atmosphere (e.g., argon) in a stable, powder form.

In this arrangement, the first kit 16 includes a third syringe 104, which contains sterile water 106 for dissolution of the powder polymer 102 just before mixing with the albumin component 100. In facilitating mixing, a stopcock valve 108 is secured to the luer fitting 88 at the dispensing end of the second dispensing syringe 62. The dispensing end 110 of the water syringe 104 couples to the stopcock valve 108, so that the water 106 can be mixed with the polymer 102 in the dispensing syringe 62 prior to use.

Figure 3:
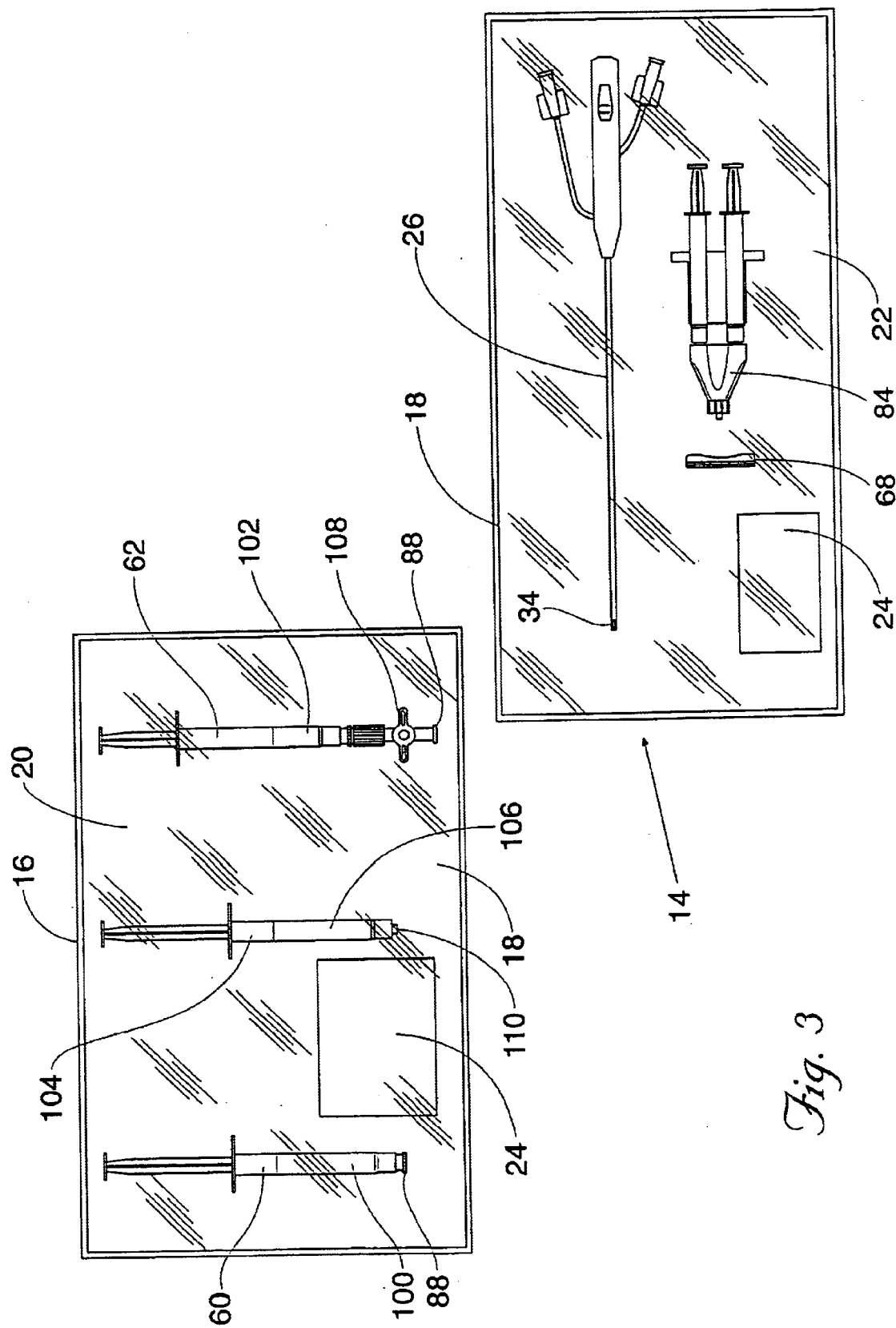
FIG. 3 is a plane view of the details of representative kits shown in FIG. 2, one kit containing the basic formative components of the genus composition, and the other kit containing a mixing/dispensing assembly for the species.
Figure 4:
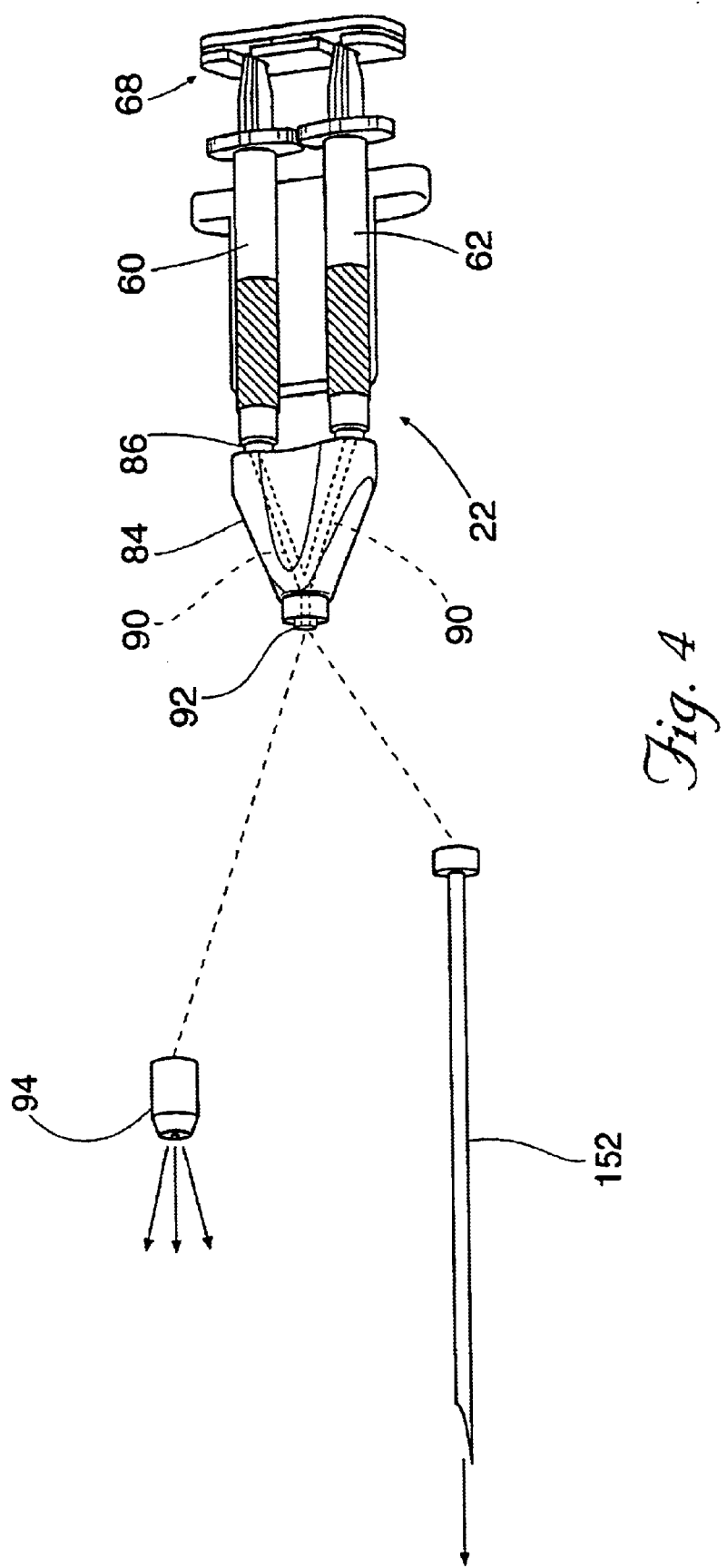
FIG. 4 is a perspective view of a representative mixing/dispensing assembly contained in the second kit shown in FIG. 3.

As FIG. 3 also shows, the second kit 18 carries the material introducer/mixer 22. As FIG. 4 shows, the two dispensing syringes 60 and 62 are snap-mounted on the material introducer/mixer 22. The material introducer/mixer 22 includes a joiner 84. The joiner 84 includes side by side female luer fittings 86. The female luer fittings 86 each receives the threaded male luer fitting 88 at the dispensing end of the dispensing syringes 60 and 62.

The joiner 84 includes interior channels 90 coupled to the female luer fittings 86. The channels 90 merge at a Y-junction into a single outlet port 92. The joiner 84 maintains two fluids dispensed by the syringes 60 and 62 separately until they leave the joiner 84. This design minimizes plugging of the joiner 84 due to a mixing reaction between the two fluids. A syringe clip 68 can be provided to ensure even application of individual solutions through the joiner 84.

The parts of the introducer/mixer 22 and joiner are made, e.g., by molding medical grade plastic materials, such as polycarbonate and acrylic.

For those therapeutic indications where the species composition needs to undergo instantaneous gelation, or gelation within a matter of a few seconds, and where the application site is exposed (e.g., Species 2, 3, 4, 5, 6, 7, 8, 9), the material introducer/mixer 22 can include a mixing spray head 94 coupled to the joiner (see FIG. 4). Preferably, the kit contains several interchangeable mixing spray heads 94, in case one mixing spray head 94 becomes clogged during use.

The mixing spray head 94 may be variously constructed and comprise a conventional spray head.

Alternatively, the material introducer/mixer 22 can include a cannula 152, which, in use, can be coupled to the joiner.

For those therapeutic indications where the species composition needs to undergo a longer period of gelation, and where access is required to a subsurface tissue site (e.g., Species 1 and 10), the material introducer/mixer 22 can include a catheter tube assembly 26 (see FIG. 3) that couples to the joiner 84. The catheter tube assembly 24 includes, at its distal end, a circumferentially spaced array of nozzles 34. The barrier material is conveyed in liquid form and dispensed in a circumferential manner through the nozzles 34 at the puncture site.

Expressed in tandem from the dispensing syringes 60 and 62, which are mechanically linked together by the joiner 84, the two fundamental components of the genus material composition come into contact in the liquid state either in the mixing spray head 94, or the cannula 152, or in the catheter tube assembly 26. Atomization of the two components occurs as they are dispersed through the mixing spray head 94. Passage of the liquid components through the cannula 152 or catheter tube will channel-mix the materials. Either by atomization or channel mixing, the liquid components are sufficiently mixed to immediately initiate the cross-linking reaction.

The material introducer/mixer 22 allows the physician to uniformly dispense the two components in a liquid state from the dispensing syringes 60 and 62. The material introducer/mixer 22 also mixes the components while flowing in the liquid state from the dispensing syringes 60 and 62.

Further details of delivery systems for those species applied by spraying on exposed tissue sites are found in U.S. patent application Ser. No. 09/283,535, filed Apr. 1, 1999, and entitled "Compositions, Systems, And Methods For Arresting or Controlling Bleeding or Fluid Leakage in Body Tissue," now U.S. Pat. No. 6,458,147 which is incorporated herein by reference.

Further details of delivery systems for those species introduced by catheter-based systems are found in U.S. patent application Ser. No. 09/188,083, filed Nov. 6, 1998 and entitled "Compositions, Systems, and Methods for Creating in Situ, Chemically Cross-linked, Mechanical Barriers," now U.S. Pat. No. 6,371,975, which is likewise incorporated herein by reference. For example, when used to deliver the Species 1 material composition, a 5.5 Fr catheter tube can be used to seal arteriotomies from 5 Fr to 10 Fr, without filling the tissue track with the Species 1 material composition. The Species 1 material composition is delivered adjacent to the arteriotomy, while the delivery device prevents the liquid from filling the tissue track. This feature ensures that the Species 1 material composition remains at the arteriotomy for maximum efficacy.

The features of the invention are set forth in the following claims.

We claim:

1. A biocompatible material comprising a mixture of a protein solution and a polymer solution including a derivative of a hydrophilic polymer with a functionality of at least three, wherein, upon mixing, the protein solution and the polymer solution cross-link to form a non-liquid, three-dimensional network that degrades over time back to a liquid form, the polymer including a degradation control region selected to achieve a desired degradation period, wherein the polymer solution comprises at least one hybrid protein.

2. A biocompatible material comprising a mixture of a protein solution and a polymer solution including a derivative of a hydrophilic polymer with a functionality of at least three, wherein, upon mixing, the protein solution and the polymer solution cross-link to form a non-liquid, three-dimensional network that degrades over time back to a liquid form, the polymer including a degradation control region selected to achieve a desired degradation period, wherein the polymer solution comprises at least one synthetic amino acid sequence.

3. A biocompatible material comprising a mixture of a protein solution and a polymer solution which, upon mixing, cross-link to form a non-liquid, three-dimensional network, and an agent that undergoes color change in response to cross-linking of the mixture.

4. A material according to claim 3 wherein the agent undergoes color change in response to change in pH.

5. A material according to claim 3 wherein the agent exhibits a first color when the mixture is in a liquid state and a second color, different than the first color, when the mixture forms the non-liquid, three-dimensional network.

6. A material according to claim 3 wherein the agent exhibits a first color when the mixture is in transition between a liquid state and the non-liquid, three dimensional network, and a second color, different than the first color, when the mixture forms the non-liquid, three-dimensional network.

7. A material according to claim 3 wherein the agent includes xylenol blue.

8. A material according to claim 3 wherein the agent includes phenol red.

9. A material according to claim 3 wherein the agent includes a mixture of xylenol blue and phenol red.

10. A material according to claim 3 wherein the agent includes phenolphthalein.

11. A material according to claim 3 wherein the agent includes o-cresolphthalein.

12. A material according to claim 3 wherein the agent includes bromothymol blue.

13. A material according to claim 3 wherein the agent includes a mixture of bromothymol blue and phenolphthalein or o-cresolphthalein.

14. A biocompatible material comprising a mixture of a protein solution and a polymer solution including a derivative of a hydrophilic polymer with a functionality of at least three, wherein, upon mixing, the protein solution and the polymer solution cross-link over time to form a non-liquid, three-dimensional network, the polymer including a cross-linking group selected to achieve a desired cross-linking period, wherein the polymer solution comprises at least one hybrid protein.

15. A biocompatible material comprising a mixture of a protein solution and a polymer solution including a derivative of a hydrophilic polymer with a functionality of at least three, wherein, upon mixing, the protein solution and the polymer solution cross-link over time to form a non-liquid, three-dimensional network, the polymer including a cross-lining group selected to achieve a desired cross-linking period, wherein the polymer solution comprises at least one synthetic amino acid sequence.

* * * * *

```
                            SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: An enzymatically degradable, collaganese
      sensitive linkage
<220> FEATURE:
<221> NAME/KEY: Unsure
<222> LOCATION: (1)..(4)
<223> OTHER INFORMATION:

<400> SEQUENCE: 1

Leu Gly Pro Ala
1
```